United States Patent
Abdur-Rashid et al.

(10) Patent No.: US 8,232,430 B2
(45) Date of Patent: Jul. 31, 2012

(54) METHOD FOR THE PREPARATION OF CIS-4-TERT-BUTYLCYCLOHEXANOL

(75) Inventors: Kamaluddin Abdur-Rashid, Mississauga (CA); Xuanhua Chen, Mississauga (CA); Rongwei Guo, Mississauga (CA); Wenli Jia, Mississauga (CA)

(73) Assignee: Kanata Chemical Technologies Inc., Toronto, Ontario (CA)

( * ) Notice: Subject to any disclaimer, the term of this patent is extended or adjusted under 35 U.S.C. 154(b) by 0 days.

(21) Appl. No.: 12/667,700

(22) PCT Filed: Jul. 7, 2008

(86) PCT No.: PCT/CA2008/001253
§ 371 (c)(1),
(2), (4) Date: May 3, 2010

(87) PCT Pub. No.: WO2009/006734
PCT Pub. Date: Jan. 15, 2009

(65) Prior Publication Data
US 2010/0204524 A1   Aug. 12, 2010

Related U.S. Application Data

(60) Provisional application No. 60/948,238, filed on Jul. 6, 2007.

(51) Int. Cl.
*C07C 35/08* (2006.01)
(52) U.S. Cl. .................................... 568/832
(58) Field of Classification Search .............. 568/832
See application file for complete search history.

(56) References Cited

U.S. PATENT DOCUMENTS 5,856,590 A   1/1999   Emura et al.

FOREIGN PATENT DOCUMENTS

| CA | 2422029 | 3/2002 |
|---|---|---|
| EP | 1 013 658 | 6/2000 |
| WO | WO 02/22526 | 3/2002 |

OTHER PUBLICATIONS

Abdur-Rashid, K.; Guo, R.; Lough, A.J.; Morris, R.H. Adv. Synth. Catal. 2005, 347, 571-579.
Clarke, Z. E. et al. Organometallics, 2006, 25:4113-4117.
Dahlenburg, L. et al. J. of Organometallic Chemistry. 2005. 690:1-13.
Doucet, H.; Ohkuma, T.; Murata, K.; Yokozawa, T.; Kozawa, M.; Katayama, E.; England, A.F.; Ikariya, T.; Noyori, R. Angew. Chem., Int. Ed. 1998, 37, 1703-1707.
Eliel, E.L.; Doyle, T.W.; Hutchins, R.O.; Gilbert, E.C. Organic Syntheses 1970, 50, 13-15.
Guo, R.; Lough, A.J.; Morris, R.H.; Song, D. Organometallics 2004, 23, 5524-5529.
Guo, R.; Lough, A.J.; Morris, A.J.; Song, D. Organometallics 2005, 24 3354-3354.
Krishnamurthy, S.; Brown, H.C. J. Am. Chem. Soc. 1976, 98, 3383-3384.
Kuhnlein, C. Den Naturwisseneschaftlichen Fakultaten der Friedrich-Alexander-Universitat Erlangen-Numberg zur Erlangung des Doctorgrades, Dec. 14, 2005.
Nishimura, S.; Ishige, M.; Shiota, M. Chemistry Letters 1977, 963-966.
Mikami, K.; Korenaga, T.; Terada, M.; Ohkuma, T.; Pham, T.; Noyori, R. Angew. Chem., Int. Ed.. 1999, 38, 495-497.
Ohkuma, T.; Ooka, H.; Ikariya, T.; Noyori, R. J. Am. Chem. Soc. 1995, 117, 10417-10418.
Ohkuma, T.; Ooka, H.; Yamakawa, M.; Ikariya, T.; Noyori, R. J. Org. Chem. 1996, 61, 4872-4873.

*Primary Examiner* — Sikarl Witherspoon
(74) *Attorney, Agent, or Firm* — Bereskin & Parr LLP/S.E.N.C.R.L., s.r.l.; Michael Fenwick

(57) ABSTRACT

The present disclosure relates to a method for the stereoselective production of cis-4-tertbutylcyclohexanol comprising contacting 4-tert-butylcyclohexanone with hydrogen gas, a catalyst comprising a ruthenium-aminophosphine complex and a base, wherein the complex is of the formula $RuX_2(PNH_2)_a(P_2)_b$ (I), wherein X is anionic ligand, $(PNH_2)$ represents an aminophosphine ligand of the formula (II) $R^1R^2P$-L-$NH_2$ and $(P_2)$ represents a diphosphine ligand of the formula (III) $R^3R^4P$-L-$PR^5R^6$.

20 Claims, 3 Drawing Sheets

METHOD FOR THE PREPARATION OF CIS-4-TERT-BUTYLCYCLOHEXANOL

This application is a national phase entry of PCT/CA2008/001253, filed Jul. 7, 2008, which claims priority from U.S. Provisional patent application Ser. No. 60/948,238 filed Jul. 6, 2007, each of these applications being incorporated herein in their entirety by reference.

FIELD OF THE DISCLOSURE

The present disclosure relates to the field of the stereoselective catalytic hydrogenations, in particular for the reduction of 4-tert-butylcyclohexanone to the corresponding alcohol, cis-4-tert-butylcyclohexanol.

BACKGROUND OF THE DISCLOSURE

Catalytic hydrogenation is a fundamental reaction in chemistry, and is used in a large number of chemical methods. Catalytic hydrogenation of ketones and aldehydes are useful and indispensable methods for the synthesis of alcohols, which are valuable end products and precursor chemicals in the pharmaceutical, agrochemical, flavor, fragrance, material and fine chemical industries.[1]

The esters of 4-tert-butylcyclohexanol, and in particular, 4-tert-butylcyclohexyl acetate, are well known perfume ingredients. Cis-4-tert-butylcyclohexyl acetate is preferred in the perfume industry because of its intense woody odor with a flowery fragrance.[2] Cis-4-tert-butylcyclohexyl acetate is obtained by acetylation of the corresponding alcohol. Various methods have been used in the industry to selectively produce cis-4-tert-butylcyclohexanol by hydrogenation of 4-tert-butylcyclohexanone. These include the use of iridium[3] and rhodium[4] catalysts or the use of bulky borohydride reagents, such as lithium trisamylborohydride.[5] However, all of these methods suffer from significant drawbacks when applied on an industrial scale, for example, due to the low substrate catalyst ratios or the use of a very reactive reagent under stoichiometric conditions.

Noyori and co-workers developed hydrogenation conditions using the $RuCl_2(PR_3)_2$(diamine) hydrogenation catalyst system.[6] Noyori and co-workers also established a method for the production of cis-4-tert-butylcyclohexanol having 95-98% selectivity using the achiral catalyst $RuCl_2(PPh_3)$(en) and similar compounds.[7]

Ruthenium aminophosphine complexes of the type $RuCl_2$(aminophosphine)$_2$ and $RuCl_2$(diphosphine)(aminophosphine) have been previously reported for the hydrogenation of ketones, aldehydes and imines.[8]

SUMMARY OF THE DISCLOSURE

It has now been found that the ruthenium aminophosphine complexes $RuCl_2$(aminophosphine)$_2$ and $RuCl_2$(diphosphine)(aminophosphine) in the presence of a base are very effective catalysts for the stereoselective hydrogenation of 4-tert-butylcyclohexanone to produce cis-4-tert-butylcyclohexanol in high yields.

Therefore, the present disclosure includes a method for the production of cis-4-tert-butylcyclohexanol comprising contacting 4-tert-butylcyclohexanone with hydrogen gas, a catalyst comprising a ruthenium-aminophosphine complex and a base.

In an aspect of the disclosure, the method is characterized by the use of a ruthenium-aminophosphine complex of the formula (I):

$$RuX_2(PNH_2)_a(P_2)_b \qquad (I)$$

wherein
X is any suitable anionic ligand and may be the same or different;
a is 1 or 2;
b is 0 or 1, where a+b=2;
($PNH_2$) represents an aminophosphine ligand of formula (II):

$$R^1R^2P\text{-}L\text{-}NH_2 \qquad (II)$$

($P_2$) represents a diphosphine ligand of the formula III $$R^3R^4P\text{-}L\text{-}PR^5R^6 \qquad (III)$$

wherein
$R^1, R^2, R^3, R^4, R^5$ and $R^6$ are simultaneously or independently selected from H, $C_{1-20}$alkyl, $C_{2-20}$alkenyl, $C_{2-20}$alkynyl, $C_{3-20}$cycloalkyl, $C_{3-20}$cycloalkenyl, $C_{6-14}$aryl, heteroaryl, $OR^7$ and $NR^7R^8$, said latter 9 groups being optionally substituted, or $R^1$ and $R^2$ and/or $R^3$ and $R^4$ and/or $R^5$ and $R^6$ are linked together to form an optionally substituted monocyclic or polycyclic ring system having 4 or more atoms, including the phosphorous atom to which said groups are bonded, and in which one or more carbon atoms in said monocyclic or polycyclic ring system is optionally replaced with a heteromoiety selected from O, S, N, $NR^7$, $SiR^7$ and $SiR^7R^8$;
L is selected from $C_{1-10}$alkylene, $C_{2-10}$-alkenylene, $C_{2-10}$alkynylene, $(C_{6-14}$arylene$)_m$, $C_{1-10}$alkylene-$C_{6-14}$arylene, $C_{6-14}$arylene-$C_{1-10}$alkylene and $C_{1-10}$alkylene-$(C_{6-14}$arylene$)_m$-$C_{1-10}$alkylene, said latter 7 groups being optionally substituted;
m is 1, 2 or 3;
the optional substituents are selected from one or more of halo, $OR^7$, $NR^7R^8$ and $R^9$; and
$R^7$ and $R^8$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl; and
$R^9$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in greater detail with reference to the following drawings in which.

DETAILED DESCRIPTION OF THE DISCLOSURE

Definitions

Figure 1:
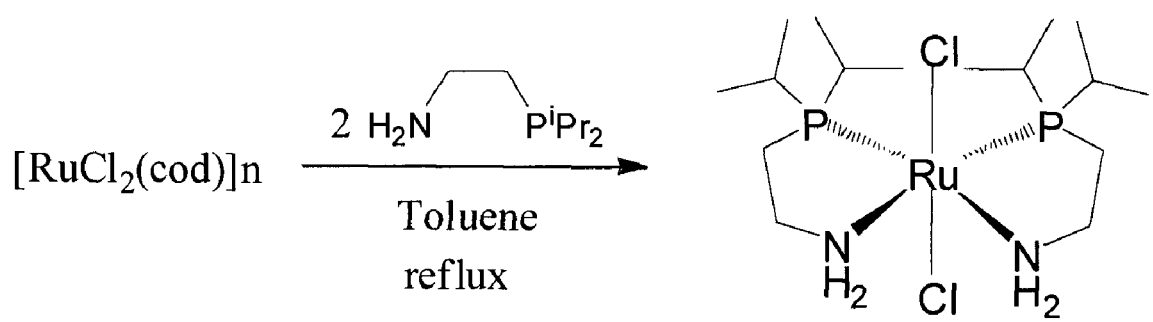
FIG. 1 shows the preparation of a ruthenium-aminophosphine complex in an embodiment of the present disclosure.

The term "$C_{1-n}$alkyl" as used herein means straight and/or branched chain, saturated alkyl groups containing from one to "n" carbon atoms and includes (depending on the identity of n) methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like, where the variable n is an integer representing the largest number of carbon atoms in the alkyl group.

The term "$C_{2-n}$alkenyl" as used herein means straight and/or branched chain, unsaturated alkyl groups containing from two to n carbon atoms and one or more, suitably one to three, double bonds, and includes (depending on the identity of n) vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like, where the variable n is an integer representing the largest number of carbon atoms in the alkenyl group.

The term "$C_{2-n}$alkynyl" as used herein means straight and/or branched chain, unsaturated alkyl groups containing from one to n carbon atoms and one or more, suitably one to three, triple bonds, and includes (depending on the identity of n) ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl-4-methylpent-2-ynyl, 1-hexynyl and the like, where the variable n is an integer representing the largest number of carbon atoms in the alkynyl group.

The term "$C_{3-n}$cycloalkyl" as used herein means a monocyclic or polycyclic saturated carbocyclic group containing from three to n carbon atoms and includes (depending on the identity of n), cyclopropyl, cyclobutyl, cyclopentyl, cyclodecyl, bicyclo[2.2.2]octane, bicyclo[3.1.1]heptane and the like, where the variable n is an integer representing the largest number of carbon atoms in the cycloalkyl group.

The term "$C_{3-n}$cycloalkenyl" as used herein means a monocyclic or polycyclic carbocyclic group containing from three to n carbon atoms and one or more, suitably one or two, double bonds and includes (depending on the identity of n), cyclopropenyl, cyclobutenyl, cyclopentenyl, cyclodecevyl, bicyclo[2.2.2]oct-2-ene, bicyclo[3.1.1]hept-2-ene and the like, where the variable n is an integer representing the largest number of carbon atoms in the cycloalkenyl group.

The term "$C_{6-n}$aryl" as used herein means a monocyclic or polycyclic carbocyclic ring system containing from 6 to n carbon atoms, at least one aromatic ring and optionally a metal and includes, depending on the identity of n, phenyl, naphthyl, anthracenyl, 1,2-dihydronaphthyl, 1,2,3,4-tetrahydronaphthyl, fluorenyl, indanyl, indenyl, ferrocenyl and the like, where the variable n is an integer representing the largest number of carbon atoms in the aryl group.

The term "heteroaryl" as used herein means a monocyclic or polycyclic ring system containing one or two aromatic rings and from 5 to 14 atoms of which, unless otherwise specified, one, two, three, four or five are heteromoieties independently selected from N, $NR^7$, $NR^7R^8$, O, S, $SiR^7$ and $SiR^7R^8$, wherein $R^7$ and $R^8$ are as defined for formula (III), and includes thienyl, furyl, pyrrolyl, pyrididyl, indolyl, quinolyl, isoquinolyl, tetrahydroquinolyl, benzofuryl, benzothienyl and the like.

The term "fluoro-substituted" with respect to any specified group as used herein means that the one or more, including all, of the hydrogen atoms in the group have been replaced with a fluorine, and includes trifluoromethyl, pentafluoroethyl, fluoromethyl and the like.

The suffix "ene" added on to any of the above groups means that the group is divalent, i.e. inserted between two other groups.

The term "ring system" as used herein refers to a carbon-containing ring system, that includes monocycles and bridged rings. Where specified, the carbons in the rings may be substituted or replaced with heteroatoms. Ring system include saturated, unsaturated or aromatic rings, or mixtures thereof.

The term "polycyclic" as used herein means groups that contain more than one ring linked together and includes, for example, groups that contain two (bicyclic), three (tricyclic) or four (quadracyclic) rings. The rings may be linked through a single bond, a single atom (spirocyclic) or through two atoms (fused and bridged).

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Method of the Disclosure

It has been found that the ruthenium aminophosphine complexes $RuCl_2(aminophosphine)_2$ and $RuCl_2(diphosphine)$ (aminophosphine) in the presence of a base are very effective catalysts for the stereoselective hydrogenation of 4-tert-butylcyclohexanone, producing cis-4-tert-butylcyclohexanol in high yields.

Accordingly, the present disclosure relates to a method for the production of cis-4-tert-butylcyclohexanol comprising contacting 4-tert-butylcyclohexanone with hydrogen gas, a catalyst comprising a ruthenium-aminophosphine complex and a base.

In an aspect of the disclosure, the method is characterized by the use of a ruthenium-aminophosphine complex of the formula (I):

$$RuX_2(PNH_2)_a(P_2)_b \qquad (I)$$

wherein
X is a suitable anionic ligand and may be the same or different;
a is 1 or 2:
b is 0 or 1, where a+b=2;
$(PNH_2)$ represents an aminophosphine ligand of formula (II):

$$R^1R^2P\text{-}L\text{-}NH_2 \qquad (II)$$

$(P_2)$ represents a diphosphine ligand of the formula III

$$R^3R^4P\text{-}L\text{-}PR^5R^6 \qquad (III)$$

wherein
$R^1$, $R^2$, $R^3$, $R^4$, $R^5$ and $R^6$ are simultaneously or independently selected from H, $C_{1-20}$alkyl, $C_{2-20}$alkenyl, $C_{2-20}$alkynyl, $C_{3-20}$cycloalkyl, $C_{3-20}$cycloalkenyl, $C_{6-14}$aryl, heteroaryl, $OR^7$ and $NR^7R^8$, said latter 9 groups being optionally substituted, or $R^1$ and $R^2$ and/or $R^3$ and $R^4$ and/or $R^5$ and $R^6$ are linked together to form an optionally substituted monocyclic or polycyclic ring system having 4 or more atoms, including the phosphorous atom to which said groups are bonded, and in which one or more carbon atoms in said monocyclic or polycyclic ring system is optionally replaced with a heteromoiety selected from O, S, N, $NR^7$, $SiR^7$ and $SiR^7R^8$;

L is selected from $C_{1-10}$alkylene, $C_{2-10}$-alkenylene, $C_{2-10}$-alkynylene, $(C_{6-14}arylene)_m$, $C_{1-10}$alkylene-$C_{6-14}$arylene, $C_{6-14}$arylene-$C_{1-10}$alkylene and $C_{1-10}$alkylene-$(C_{6-14}$arylene$)_m$-$C_{1-10}$alkylene, said latter 7 groups being optionally substituted;

m is 1, 2 or 3;

the optional substituents are selected from one or more of halo, $OR^7$, $NR^7R^8$ and $R^9$; and $R^7$ and $R^8$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl; and $R^9$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl.

In the present disclosure, a is equal to 1 or 2 and b is equal to 0 or 1, wherein a+b=2. In embodiments of the disclosure, a is equal to 2.

In an embodiment of the present disclosure $R^1$, $R^2$, $R^3$, $R^4$, $R^5$ and $R^6$ are simultaneously or independently selected from H, $C_{1-10}$alkyl, $C_{2-10}$-alkenyl, $C_{2-10}$alkynyl, $C_{3-10}$cycloalkyl, $C_{3-10}$cycloalkenyl, $C_{6-10}$-aryl, heteroaryl, $OR^7$ and $NR^7R^8$, said latter 9 groups being optionally substituted, or $R^1$ and $R^2$ and/or $R^3$ and $R^4$ and/or $R^5$ and $R^6$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or polycyclic ring system is optionally replaced with a heteromoiety selected from O, S, N, NH and $NC_{1-4}$alkyl. In a further embodiment, $R^1$, $R^2$, $R^3$, $R^4$, $R^5$ and $R^6$ are simultaneously or independently selected from H, $C_{1-6}$alkyl, $C_{2-6}$alkenyl, $C_{2-6}$alkynyl, $C_{3-6}$cycloalkyl, $C_{3-6}$cycloalkenyl and $C_{6-10}$aryl said latter 6 groups being optionally substituted, or $R^1$ and $R^2$ and/or $R^3$ and $R^4$ and/or $R^5$ and $R^6$ are linked together to form an optionally substituted monocyclic or bicyclic, saturated, unsaturated and/or aromatic ring system having 4 to 10 atoms, including the phosphorous atom to which said groups are bonded. In another embodiment of the disclosure $R^1$, $R^2$, $R^3$, $R^4$, $R^5$ and $R^6$ are simultaneously or independently selected from H, $C_{1-6}$alkyl, $C_{2-6}$alkenyl, $C_{2-6}$alkynyl, $C_{3-6}$cycloalkyl, and $C_{6-10}$aryl said latter 6 groups being optionally substituted, or $R^1$ and $R^2$ and/or $R^3$ and $R^4$ and/or $R^5$ and $R^6$ are linked together to form an optionally substituted monocyclic or bicyclic, saturated, unsaturated and/or aromatic ring system having 4 to 10 atoms, including the phosphorous atom to which said groups are bonded. In specific embodiments of the disclosure, $R^1$, $R^2$, $R^3$, $R^4$, $R^5$ and $R^6$ are simultaneously or independently selected from phenyl and $C_{1-6}$alkyl, suitably, phenyl, methyl, ethyl, n-propyl, isopropyl, sec-butyl, tert-butyl and n-butyl.

In an embodiment of the disclosure, L is selected from $C_{1-6}$alkylene, $C_{2-6}$alkenylene and $(C_{6-14}arylene)_m$, said latter 3 groups being optionally substituted and m is 1 or 2. In a further embodiment L is unsubstituted $C_{1-6}$alkylene, suitably unsubstituted $C_{1-4}$alkylene, more suitably unsubstituted $C_{2-3}$alkylene. In a further embodiment, L is optionally substituted biphenyl or binaphthyl, more suitably unsubstituted biphenyl or binaphthyl. In another embodiment of the disclosure the biphenyl has a bond between the 2 and 2' positions and the binaphthyl has a bond between the 2 and 2' positions.

According to embodiments of the disclosure, the optional substituents on the aminophosphine and diphosphine ligands of formulae II and III are selected from one or more of halo, OH, $NH_2$, $NHR^7$, $OR^7$, $N(R^7)(R^8)$ and $R^9$, in which $R^7$, $R^8$ and $R^9$ are simultaneously or independently selected from fluoro-substituted-$C_{1-6}$alkyl, $C_{1-6}$alkyl, $C_{2-6}$alkenyl, $C_{2-6}$alkynyl and $C_{6-14}$aryl. In embodiments of the disclosure, the optional substituents are selected from one or more of halo, OH, $NH_2$, $NHR^7$, $OR^7$, $NR^7R^8$ and $R^9$, in which $R^7$, $R^8$ and $R^9$ are simultaneously or independently selected from fluoro-substituted-$C_{1-4}$alkyl, $C_{1-4}$alkyl, $C_{2-4}$alkenyl and phenyl, specifically methyl and phenyl.

The ligands X may be the same or different and are selected from any anionic ligand, suitably halo (for example, fluoro, chloro, bromo or iodo, specifically chloro), $HO^-$, $R^9O^-$ and $R^9C(O)^-$, wherein $R^9$ is H or $C_{1-6}$alkyl. In an embodiment of the disclosure, X is chloro.

In a general way, the complexes of the aminophosphine and diphosphine ligands of formulae II and III can be prepared and isolated prior to their use in the method according to the general methods described in the literature (see for example, Clarke, Z. E. et al. Organometallics, 2006, 25:4113-4117) or using the methods described herein.

The ruthenium complexes of formula (I) can catalytically hydrogenate 4-tertbutylcyclohexanone in the presence of a base. The base can be any conventional base and one can cite, as non-limiting examples, organic non-coordinating bases such as DBU, an alkaline or alkaline-earth metal carbonate, a carboxylate salt such as sodium or potassium acetate, or an alcoholate or hydroxide salt. In an embodiment of the disclosure, the bases are the alcoholate or hydroxide salts selected from the compounds of formula $(R^{10}O)_2M'$ and $R^{10}OM'$, wherein M' is an alkaline or alkaline-earth metal and $R^{10}$ stands for hydrogen or a linear or branched alkyl group. In a further embodiment of the disclosure, $R^{10}$ is t-butyl and M' is potassium.

Standard catalytic hydrogenation conditions, as used herein, typically implies the mixture of the substrate with a ruthenium-aminophosphine compound of formula (I) in the presence of a base, with a solvent, and then treating such a mixture with a hydrogen gas at a chosen pressure and temperature.

In an embodiment of the disclosure the hydrogen gas is used at a pressure of about 1 atm to about 100 atm, suitably about 7 atm to about 13 atm, more suitably about 10 atm.

The complexes of formula (I) can be added to the reaction medium in a large range of concentrations. As non-limiting examples, one can cite as complex concentration values those ranging from 0.1 ppm to 50,000 ppm, relative to the amount of substrate, thus representing respectively a substrate/complex (S/com or S/C) ratio of $10^7$ to 20. In an embodiment of the disclosure, the complex concentration will be comprised between 0.1 and 1000 ppm, i.e. a S/com ratio of $10^7$ to 1000 respectively. In a further embodiment of the disclosure, there will be used concentrations in the range of 0.5 to 100 ppm, corresponding to a S/com ratio of 10,000 to $2 \times 10^6$ respectively.

In an embodiment of the disclosure, the base may be included in a relatively large range. One can cite, as non-limiting examples, ranges between 1 to 50,000 molar equivalents relative to the complex (e.g. base/com=0.5 to 50,000), or 100 to 20,000, or even between 400 and 10,000 molar equivalents. However, it should be noted that it is also possible to add a small amount of base (e.g. base/com=1 to 3) to achieve high yields.

In an embodiment of the present disclosure, the catalytic hydrogenation reaction is carried out in the presence of a solvent. A wide variety of solvents can be used for the catalytic hydrogenation. Non-limiting examples include aromatic solvents such as benzene, toluene or xylene, hydrocarbon solvents such as hexane or cyclohexane, ethers and esters such as tetrahydrofuran, diethyl ether and ethyl acetate, primary or secondary alcohols such as methanol, ethanol and isopropanol, chlorinated solvents such as dichloromethane and chloroform, or mixtures thereof.

The temperature at which the catalytic hydrogenation can be carried out is comprised between about 0° C. and about 100° C., more specifically in the range of between about 20° C. and about 80° C. In an embodiment of the disclosure, the catalytic hydrogenation is carried out at about room temperature. Of course, a person skilled in the art is also able to select the temperature as a function of the melting and boiling point of the starting and final products.

The following non-limiting examples are illustrative of the present disclosure:

EXAMPLES

All preparations and manipulations were carried out under hydrogen or argon atmospheres with the use of standard Schlenk, vacuum line and glove box techniques in dry, oxygen-free solvents. Tetrahydrofuran (THF), diethyl ether ($Et_2O$) and hexanes were purified and dried using an Innovative Technologies solvent purification system. Deuterated solvents were degassed and dried before use. Potassium tert-butoxide, aldehydes and ketones were supplied by Aldrich Chemical Company. NMR spectra were recorded on either a Varian Unity Inova 300 MHz spectrometer (300 MHz for $^1H$, 75 MHz for $^{13}C$ and 121.5 for $^{31}P$) or a Bruker Avance 500 MHz DRX spectrometer. All $^{31}P$ chemical shifts were measured relative to 85% $H_3PO_4$ as an external reference. The $^1H$ and $^{13}C$ chemical shifts were measured relative to partially deuterated solvent peaks but are reported relative to tetramethylsilane. The alcohol products obtained from the catalytic hydrogenation of ketones were characterized by their $^1H$ and $^{13}C$ NMR spectra. The aminophosphine ligands $^iPr_2PCH_2CH_2NH_2$ and $Ph_2PCH_2CH_2NH_2$, and the ruthenium complexes $RuCl_2(Ph_2PCH_2CH_2NH_2)_2$, $RuCl_2(R$-binap$)(Ph_2PCH_2CH_2NH_2)$ and $RuCl_2(^iPr_2PCH_2CH_2NH_2)_2$ are commercially available from Kanata Chemical Technologies Inc.

Example 1

Preparation of $RuCl_2(^iPr_2PCH_2CH_2NH_2)_2$ (3)

A mixture of $RuCl_2(cod)]_n$ (1.0 mmol) and the aminophosphine ligand $^iPr_2PCH_2CH_2NH_2$ (2.1 mmol) was refluxed in toluene (40 ml) under argon for 12 hours. The mixture was cooled to room temperature and stirred for 6 hours. Ether (100 ml) was added, and the mixture stirred for 2 hours. The product was filtered, washed with ether (3×10 ml), and dried under vacuum. Yield=93%. $^1H$ NMR ($CD_2Cl_2$), d: 1.17-1.38 (m, 24H, $CH_3$); 2.00 (m, 4H, $CH_2$); 2.52 (doublet of septet, $J_{HP}$=9.3 Hz, $J_{HH}$=10.5 Hz, 4H, CH); 3.06 (m, 4H, $CH_2$); 3.65 (br, 4H, NH). $^{31}P\{^1H\}$ NMR ($CD_2Cl_2$), d: 64.2 (s).

Example 2

General Procedure for Catalytic Hydrogenation of Ketones and Aldehydes

In a typical catalytic hydrogenation procedure, a weighed amount of the respective ruthenium catalyst and KO$^t$Bu were added to a solution of the substrate in 2-propanol under hydrogen gas. The pressure was adjusted to the desired value and the reaction progress was monitored using TLC or NMR. After completion of the reaction, the solvent was removed by evaporation under reduced pressure. The alcohols were purified by filtering a hexane solution of the crude product through a pad of silica, then removing the hexane under reduced pressure. The conversion and purity of the alcohol products was assessed using NMR.

Discussion

The ruthenium aminophosphine complexes $RuCl_2(Ph_2PCH_2CH_2NH_2)_2$ (1) and $RuCl_2(R$-binap$)(Ph_2PCH_2CH_2NH_2)$ (2) were prepared as previously described.[7] Table 1 shows the hydrogenation of ketones using the ruthenium-aminophosphine complex, $RuCl_2(i$-$Pr_2PCH_2CH_2NH_2)_2$ (3), to prove its efficacy as a catalyst for hydrogenation.

Figure 2:
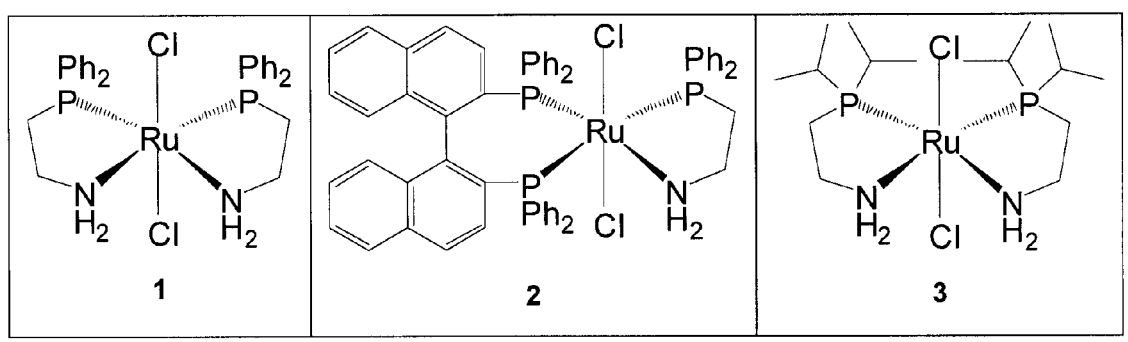
FIG. 2 shows the structure of ruthenium complexes in embodiments of the disclosure.
Figure 3:
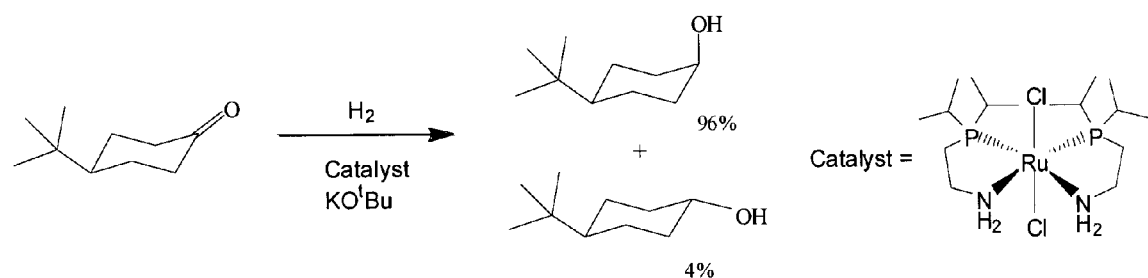
FIG. 3 shows the reduction of 4-tertbutylcyclohexanol in an embodiment of the disclosure.

Table 2 shows the hydrogenation of 4-tert-butylcyclohexanone using catalysts (1), (2) and (3) (see FIG. 2) in the presence of a base. Catalyst (3) shows a cis:trans selectivity of 96:4 for the production of cis-4-tert-butylcyclohexanol.

The results show that the ruthenium-aminophosphine complexes of the present disclosure represent a very effective class of catalysts for hydrogenation of 4-tert-butyl cyclohexanone. The ketone was readily converted to the alcohol using each of the complexes (1, 2 and 3) as catalyst in the presence of base. Good selectivity was obtained for the desired cis-4-tert-butyl cyclohexanol, in particular with catalyst 3.

Example 3

Catalytic Hydrogenation of 4-tert-butylcyclohexanone with $RuCl_2(i$-$Pr_2PCH_2CH_2NH_2)_2$ (3)

(a) Substrate:Catalyst Ratio of 10,000:1

A weighed amount of the catalyst (3.2 mg, 0.0065 mmol) and KO$^t$Bu (100 mg) were added to a solution of the substrate (10.0 g, 65 mmol) in 2-propanol in a 100 ml Parr pressure reactor under a flow of argon. The mixture was de-gassed with argon and then with hydrogen. It was finally pressurized to 10 atm. of hydrogen and stirred at the desired temperature. Yields are based on the amount of substrate and are shown in Table 3.

(b) Substrate:Catalyst Ratio of 100,000:1

A weighed amount of the catalyst (5 mg) was dissolved in 10.0 ml of 2-propanol. An aliquot of 1.0 ml of the diluted catalyst solution (0.5 mg of catalyst, 0.001 mmol) and KO$^t$Bu (150 mg) were added to a solution of the substrate (15.6 g, 101 mmol) in 2-propanol in a 100 ml Parr pressure reactor under a flow of argon. The mixture was de-gassed with argon and then with hydrogen. It was finally pressurized to 10 atm. of hydrogen and stirred at the desired temperature. Yields are based on the amount of substrate and are shown in Table 3.

(c) Substrate:Catalyst Ratio of 500,000:1

A weighed amount of the catalyst (5 mg) was dissolved in 10.0 ml of 2-propanol. An aliquot of 1.0 ml of this catalyst solution was further diluted to 10.0 ml with 2-propanol. An aliquot of 2.0 ml of the dilute catalyst solution (0.1 mg, 0.0002 mmol) and KO$^t$Bu (150 mg) were added to a solution of the substrate (15.6 g, 101 mmol) in 2-propanol in a 100 ml Parr pressure reactor under a flow of argon. The mixture was de-gassed with argon and then with hydrogen. It was finally pressurized to 10 atm. of hydrogen and stirred at the desired temperature. Yields are based on the amount of substrate.

(d) Substrate:Catalyst Ratio of 1,000,000:1

A weighed amount of the catalyst (5 mg) was dissolved in 10.0 ml of 2-propanol. An aliquot of 1.0 ml of this catalyst solution was further diluted to 10.0 ml with 2-propanol. An aliquot of 1.0 ml of the dilute catalyst solution (0.05 mg, 0.0001 mmol) and KO$^t$Bu (150 mg) were added to a solution of the substrate (15.6 g, 101 mmol) in 2-propanol in a 100 ml Parr pressure reactor under a flow of argon. The mixture was de-gassed with argon and then with hydrogen. It was finally pressurized to 10 atm. of hydrogen and stirred at the desired temperature. Yields are based on the amount of substrate.

Discussion

Table 3 shows the hydrogenation of 4-tert-butylcyclohexanone using catalyst (3) in varying substrate:catalyst ratios, in the presence of a base. Catalyst (3) shows a cis:trans selectivity of at least 95:5 for the production of cis-4-tert-butylcyclohexanol, and 100% conversion for the 10,000/100,000/500,000:1 ratios of substrate:catalyst.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

HYDROGENATION OF KETONES USING $RuCl_2(i-Pr_2PCH_2CH_2NH_2)_2$/t-BuOK (1:10) AS CATALYST IN 2-PROPANOL (10 ATM. $H_2$) AT ROOM TEMPERATURE.[a]

| entry | substrate | S:C | time (h) | conv (%) |
|---|---|---|---|---|
| 1 | | 5000 | 1.5 | 100 |
| 4[b] | | 500 | 3 | 100 |
| 6[c] | | 650 | 6 | 100 |

[a]A weighed amount of the catalyst and KO$^t$Bu were added to a solution of the substrate in 2-propanol and the mixture stirred at room temperature under hydrogen gas. Yields are based on the amount of substrate.
[b]Only carbonyl group is reduced;
[c]ratio of endo:exo = 87:13.

TABLE 2

HYDROGENATION OF 4-TERT-BUTYLCYCLOHEXANONE USING 1, 2 AND 3 AS CATALYST IN 2-PROPANOL (10 ATM. $H_2$) AT ROOM TEMPERATURE.[a]

| entry | catalyst | S:C | time (h) | conv (%) | cis:trans |
|---|---|---|---|---|---|
| 1 | 1 | 1000 | 2 | 100 | 86:14 |
| 2 | 2 | 1000 | 6 | 100 | 90:10 |
| 3 | 3 | 1000 | 2 | 100 | 96:4 |

[a]A weighed amount of the catalyst and KO$^t$Bu were added to a solution of the substrate in 2-propanol and the mixture stirred at room temperature under hydrogen gas. Yields are based on the amount of substrate.

TABLE 3

HYDROGENATION OF 4-TERT-BUTYLCYCLOHEXANONE USING 3 AS CATALYST IN 2-PROPANOL (10 ATM. $H_2$).

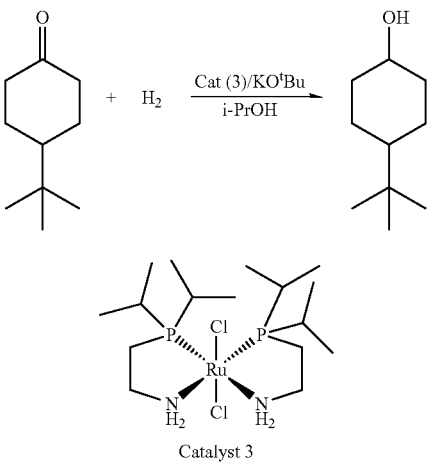

Catalyst 3

| Entry | S:C | Temp. (° C.) | Time (h) | Conv. (%) | Cis/Trans |
|---|---|---|---|---|---|
| 1 | 10,000 | 20 | 4 | 100 | 96/4 |
| 2 | 100,000 | 50 | 2 | 100 | 95/5 |
| 3 | 500,000 | 50 | 12 | 100 | 95/5 |
| 4 | 1,000,000 | 50 | 24 | 80 | 95/5 |

FULL CITATIONS FOR DOCUMENTS REFERRED TO IN THE SPECIFICATION (1) (a) Mikami, K.; Korenaga, T.; Terada, M.; Ohkuma, T.; Pham, T.; Noyori, R. *Angew. Chem., Int. Ed.* 1999, 38, 495-497. (b) Doucet, H.; Ohkuma, T.; Murata, K.; Yokozawa, T.; Kozawa, M.; Katayama, E.; England, A. F.; Ikariya, T.; Noyori, R. *Angew. Chem., Int. Ed.* 1998, 37, 1703-1707. (c) Ohkuma, T.; Ooka, H.; Ikariya, T.; Noyori, R. *J. Am. Chem. Soc.* 1995, 117, 10417-10418.

(2) Arctander, S. 1969, *Perfume and Flavor Chemicals*, Montclair, N.J., Monograph No. 441.

(3) Eliel, E. L.; Doyle, T. W.; Hutchins, R. O.; Gilbert, E. C. *Organic Syntheses* 1970, 50, 13-15.

(4) Nishimura, S.; Ishige, M.; Shiota, M. *Chemistry Letters* 1977, 963-966.

(5) Krishnamurthy, S.; Brown, H. C. *J. Am. Chem. Soc.* 1976, 98, 3383-3384.

(6) (a) Mikami, K.; Korenaga, T.; Terada, M.; Ohkuma, T.; Pham, T.; Noyori, R. *Angew. Chem., Int. Ed.* 1999, 38, 495-497. (b) Ohkuma, T.; Ooka, H.; Ikariya, T.; Noyori, R. *J. Am. Chem. Soc.* 1995, 117, 10417-10418.

(7) (a) Doucet, H.; Ohkuma, T.; Murata, K.; Yokozawa, T.; Kozawa, M.; Katayama, E.; England, A. F.; Ikariya, T.; Noyori, R. *Angew. Chem., Int. Ed.* 1998, 37, 1703-1707. (b) Ohkuma, T.; Ooka, H.; Yamakawa, M.; Ikariya, T.; Noyori, R. *J. Org. Chem.* 1996, 61, 4872-4873. (c) U.S. Pat. No. 5,856,590, 1999.

(8) (a) PCT Int. Appl. WO 02/22526 A2. (b) Abdur-Rashid, K.; Guo, R.; Lough, A. J.; Morris, R. H. *Adv. Synth. Catal.* 2005, 347, 571-579. (c) Guo, R.; Lough, A. J.; Morris, R. H.; Song, D. *Organometallics* 2004, 23, 5524-5529. (d) Guo, R.; Lough, A. J.; Morris, A. J.; Song, D. *Organometallics* 2005, 24 3354-3354.

We claim:

1. A method for the production of cis-4-tertbutylcyclohexanol comprising contacting 4-tert-butylcyclohexanone with hydrogen gas, a catalyst comprising a ruthenium-aminophosphine complex and a base, wherein the complex is of the formula (I):

$$RuX_2(PNH_2)_a(P_2)_b \qquad (I)$$

wherein

X is a suitable anionic ligand and may be the same or different;

a is 1 or 2:

b is 0 or 1, where a+b=2;

(PNH$_2$) represents an aminophosphine ligand of formula (II):

$$R^1R^2P\text{-}L\text{-}NH_2 \qquad (II)$$

(P$_2$) represents a diphosphine ligand of the formula III $$R^3R^4P\text{-}L\text{-}PR^5R^6 \qquad (III)$$

wherein $R^1$, $R^2$, $R^3$, $R^4$, $R^5$ and $R^6$ are simultaneously or independently selected from H, $C_{1-20}$alkyl, $C_{2-20}$alkenyl, $C_{2-20}$alkynyl, $C_{3-20}$cycloalkyl, $C_{3-20}$cycloalkenyl, $C_{6-14}$aryl, heteroaryl, $OR^7$ and $NR^7R^8$, said latter 9 groups being optionally substituted, or $R^1$ and $R^2$ and/or $R^3$ and $R^4$ and/or $R^5$ and $R^6$ are linked together to form an optionally substituted monocyclic or polycyclic ring system having 4 or more atoms, including the phosphorous atom to which said groups are bonded, and in which one or more carbon atoms in said monocyclic or polycyclic ring system is optionally replaced with a heteromoiety selected from O, S, N, $NR^7$, $SiR^7$ and $SiR^7R^8$;

L is selected from $C_{1-10}$alkylene, $C_{2-10}$alkenylene, $C_{2-10}$alkynylene, $(C_{6-14}$arylene$)_m$, $C_{1-10}$alkylene-$C_{6-14}$arylene, $C_{6-14}$arylene-$C_{1-10}$alkylene and $C_{1-10}$alkylene-$(C_{6-14}$arylene$)_m$-$C_{1-10}$alkylene, said latter 7 groups being optionally substituted;

m is 1, 2 or 3;

the optional substituents are selected from one or more of halo, $OR^7$, $NR^7R^8$ and $R^9$; and $R^7$ and $R^8$ are simultaneously or independently selected from H, fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl; and $R^9$ is selected from fluoro-substituted-$C_{1-6}$alkyl, $C_{1-6}$alkyl, $C_{2-6}$alkenyl, $C_{2-6}$alkynyl, $C_{6-14}$aryl and $C_{1-6}$alkylene-$C_{6-14}$aryl, wherein the cis-4-tertbutylcyclohexanol is prepared having a cis:trans ratio of 80:20 or more with respect to the cis isomer.

2. The method according to claim 1, wherein a is equal to 2.

3. The method according to claim 1, wherein $R^1$, $R^2$, $R^3$, $R^4$, $R^5$ and $R^6$ are simultaneously or independently selected from H, $C_{2-10}$alkenyl, $C_{2-10}$alkynyl, $C_{3-10}$cycloalkyl, $C_{3-10}$cycloalkenyl, $C_{6-10}$aryl, heteroaryl, $OR^7$ and $NR^7R^8$, said latter 9 groups being optionally substituted, or $R^1$ and $R^2$ and/or $R^3$ and $R^4$ and/or $R^5$ and $R^6$ are linked together to form an optionally substituted monocyclic or bicyclic, saturated, unsaturated and/or aromatic ring system having 4 to 14 atoms, including the phosphorous atom to which said groups are bonded, and in which one or more carbon atoms in said monocyclic or polycyclic ring system is optionally replaced with a heteromoiety selected from O, S, N, NH and $NC_{1-4}$alkyl.

4. The method according to claim 3, wherein $R^1$, $R^2$, $R^3$, $R^4$, $R^5$ and $R^6$ are simultaneously or independently selected from H, $C_{1-6}$alkyl, $C_{2-6}$alkenyl, $C_{2-6}$alkynyl, $C_{3-6}$cycloalkyl, $C_{3-6}$cycloalkenyl and $C_{6-10}$aryl said latter 6 groups being optionally substituted, or $R^1$ and $R^2$ and/or $R^3$ and $R^4$ may be linked together to form an optionally substituted monocyclic or bicyclic, saturated, unsaturated and/or aromatic ring system having 4 to 10 atoms, including the phosphorous atom to which said groups are bonded.

5. The method according to claim 4, wherein $R^1$, $R^2$, $R^3$, $R^4$, $R^5$ and $R^6$ are simultaneously or independently selected from H, $C_{1-6}$alkyl, $C_{2-6}$alkenyl, $C_{2-6}$alkynyl, $C_{3-6}$cycloalkyl, and $C_{6-10}$aryl said latter 6 groups being optionally substituted, or $R^1$ and $R^2$ and/or $R^3$ and $R^4$ and/or $R^5$ and $R^6$ are linked together to form an optionally substituted monocyclic or bicyclic, saturated, unsaturated and/or aromatic ring system having 4 to 10 atoms, including the phosphorous atom to which said groups are bonded.

6. The method according to claim 5, wherein $R^1$, $R^2$, $R^3$, $R^4$, $R^5$ and $R^6$ are simultaneously or independently selected from phenyl and $C_{1-6}$alkyl.

7. The method according to claim 5, wherein $R^1$, $R^2$, $R^3$, $R^4$, $R^5$ and $R^6$ are simultaneously or independently selected phenyl, methyl, ethyl, n-propyl, isopropyl, sec-butyl, tert-butyl and n-butyl.

8. The method according to claim 1, wherein L is selected from $C_{1-6}$alkylene, $C_{2-6}$alkenylene and $(C_{6-14}$arylene$)_m$, said latter 3 groups being optionally substituted and m is 1 or 2.

9. The method according to claim 8, wherein L is unsubstituted $C_{1-6}$alkylene.

10. The method according to claim 9, wherein L is unsubstituted $C_{1-4}$alkylene.

11. The method according to claim 10, wherein L is unsubstituted $C_{2-4}$alkylene.

12. The method according to claim 8, wherein L is optionally substituted biphenyl or binaphthyl.

13. The method according to claim 12, wherein L is unsubstituted biphenyl or binaphthyl.

14. The method according to claim 12, wherein the biphenyl has a bond between the 2 and 2' positions and the binaphthyl has a bond between the 2 and 2' positions.

15. The method according to claim 1, wherein the optional substituents on the aminophosphine and diphosphine ligands of formulae II and III are selected from one or more of halo, OH, $NH_2$, $NHR^7$, $OR^7$, $NR^7R^8$ and $R^9$, in which $R^7$, $R^8$ and $R^9$ are simultaneously or independently selected from fluoro-substituted-$C_{1-4}$alkyl, $C_{1-4}$alkyl, $C_{2-4}$alkenyl and phenyl.

16. The method according to claim 1, wherein X may be the same or different and are selected from halo, $R^9C(O)O^-$, $HO^-$ and $R^9O^-$ wherein $R^9$ is H or $C_{1-6}$alkyl.

17. The method according to claim 1, wherein the base is an organic non-coordinating base, an alkaline or alkaline-earth metal carbonate, a carboxylate salt or an alcoholate or hydroxide salt.

18. The method according to claim 1, wherein the tert-butylcyclohexanone is contacted with hydrogen gas, a catalyst comprising a ruthenium-aminophosphine complex and a base in a solvent selected from benzene, toluene, xylene, hexane, cyclohexane, tetrahydrofuran, diethyl ether, primary or secondary alcohols, chlorinated solvents and mixtures thereof.

19. The method according to claim 1, wherein the hydrogen gas is used at a pressure of about 1 atm to about 100 atm.

20. The method according to claim 19, wherein the hydrogen gas is used at a pressure about 7 atm to about 13 atm.

* * * * *

UNITED STATES PATENT AND TRADEMARK OFFICE
CERTIFICATE OF CORRECTION

PATENT NO. : 8,232,430 B2
APPLICATION NO. : 12/667700
DATED : July 31, 2012
INVENTOR(S) : Kamaluddin Abdur-Rashid et al.

It is certified that error appears in the above-identified patent and that said Letters Patent is hereby corrected as shown below:

Column 11, line 54, insert --$C_{1-10}$alkyl,-- before --$C_{2-10}$alkenyl,--;

Signed and Sealed this
Ninth Day of October, 2012

David J. Kappos
*Director of the United States Patent and Trademark Office*